(12) United States Patent
Khang et al.

(10) Patent No.: US 7,814,933 B2
(45) Date of Patent: Oct. 19, 2010

(54) APPARATUS AND METHOD FOR STABILIZING CONCENTRATION OF AEROSOL

(75) Inventors: Yoon-ho Khang, Gyeonggi-do (KR);
Joo-hyun Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 1167 days.

(21) Appl. No.: 10/998,043

(22) Filed: Nov. 29, 2004

(65) Prior Publication Data

US 2005/0118110 A1    Jun. 2, 2005

(30) Foreign Application Priority Data

Nov. 29, 2003    (KR)   ................. 10-2003-0086045

(51) Int. Cl.
    *B01F 15/02*    (2006.01)
(52) U.S. Cl. .................. 137/563; 137/888; 239/124; 366/137
(58) Field of Classification Search ................ 137/563, 137/888, 892, 893, 894, 895; 222/318, 402.1; 239/124; 366/136, 137
See application file for complete search history.

(56) References Cited

U.S. PATENT DOCUMENTS

| | | | | |
|---|---|---|---|---|
| 1,947,851 A | * | 2/1934 | Jewett | .................. 366/136 |
| 3,558,052 A | * | 1/1971 | Dunn | ..................... 239/124 |
| 3,870,228 A | * | 3/1975 | Moseley, Jr. | .............. 137/893 |
| 3,901,184 A | * | 8/1975 | Payne et al. | ............... 239/124 |
| 4,834,782 A | * | 5/1989 | Silva | ........................ 137/563 |
| 5,334,496 A | * | 8/1994 | Pond et al. | ................. 366/136 |
| 7,134,618 B2 | * | 11/2006 | Harutyunyan et al. | ....... 222/318 |

FOREIGN PATENT DOCUMENTS

JP      05-317671      12/1993

OTHER PUBLICATIONS

Official Action (Notice to Submit Response) issued by the Korean Intellectual Property Office in priority Korean Application No. 10-2003-0086045 on Aug. 24, 2006, and English translation thereof.

* cited by examiner

*Primary Examiner*—John Rivell
(74) *Attorney, Agent, or Firm*—Cantor Colburn LLP

(57) ABSTRACT

Provided is an apparatus for stabilizing the concentration of a previously generated aerosol, which includes: an aerosol inlet channel; an aerosol pressure adjustment unit accelerating the aerosol; a buffer connected to the aerosol pressure adjustment unit via an aerosol transport channel and having a much larger sectional area than the aerosol inlet channel and the aerosol transport channel, wherein the aerosol accelerated by the aerosol pressure adjustment unit reaches the buffer via the aerosol transport channel and is mixed in the buffer; a feedback channel connecting between the buffer and the preceding channel to the buffer to feedback a portion of the aerosol present in the buffer to the preceding channel to the buffer; and an aerosol outlet channel releasing the aerosol uniformly mixed in the buffer. Provided is also a method for stabilizing the concentration of an aerosol according to the same principle as in the apparatus.

4 Claims, 2 Drawing Sheets

APPARATUS AND METHOD FOR STABILIZING CONCENTRATION OF AEROSOL

This application claims priority from Korean Patent Application No. 2003-86045, filed on Nov. 29, 2003, in the Korean Intellectual Property Office, the disclosure of which is incorporated herein in its entirety by reference.

BACKGROUND OF THE INVENTION

1. Field of the Invention

The present invention relates to a method and an apparatus for making uniform an aerosol concentration that changes with time of aerosol generation.

2. Description of the Related Art

Various methods for generating an aerosol containing solid powders or liquid droplets are currently known. In particular, generation of an aerosol from a solid powder is accomplished by a fluidized bed method, scraping of the powder packed in cylindrical shape, and the like. In generation of a powder aerosol, to uniformly maintain the concentration of powders in the aerosol, a uniform supply of source powders and an efficient conversion of the supplied source powders to an aerosol form are required.

However, according to currently available aerosol generation methods, an aerosol concentration is not constant over time. In detail, according to these methods, an average aerosol concentration over an extended period of time can be maintained constant, but it is very difficult to accomplish a short-term concentration stability of an aerosol.

In a process of using an aerosol, it is common to use solid powders or liquid droplets contained in the aerosol as a process material. In this regard, the concentration of the aerosol corresponds to the quantity of the process material. Therefore, uniform maintenance of the quantity of the process material with time by stabilization of the aerosol concentration is very important for process stabilization.

Therefore, a method for stabilizing an aerosol concentration that changes with time of aerosol generation is required.

SUMMARY OF THE INVENTION

The present invention provides an apparatus for stabilizing an aerosol concentration that changes with time of aerosol generation.

The present invention also provides a method for stabilizing an aerosol concentration that changes aerosol generation over time.

According to an aspect of the present invention, there is provided an apparatus for stabilizing the concentration of a previously generated aerosol, which includes: an aerosol inlet channel; an aerosol pressure adjustment unit accelerating the aerosol; a buffer connected to the aerosol pressure adjustment unit via an aerosol transport channel and having a much larger sectional area than the aerosol inlet channel and the aerosol transport channel, wherein the aerosol accelerated by the aerosol pressure adjustment unit reaches the buffer via the aerosol transport channel and is mixed in the buffer; a feedback channel connecting between the buffer and the preceding channel to the buffer to feedback a portion of the aerosol present in the buffer to the preceding channel to the buffer; and an aerosol outlet channel releasing the aerosol uniformly mixed in the buffer.

The aerosol pressure adjustment unit may be a Venturi tube. The pressure of the Venturi tube must be lower than that of the buffer.

The buffer may have a capacity that corresponds to the volume of the aerosol that passes through the aerosol inlet channel and the aerosol transport channel for a period of 0.1 to 100 times of a concentration change period of the aerosol.

According to another aspect of the present invention, there is provided a method for stabilizing the concentration of a previously generated aerosol, which includes: supplying the aerosol into a channel; accelerating the aerosol by a pressure adjustment unit; supplying the aerosol into a buffer having a much larger sectional area than the channel; feedbacking a portion of the aerosol in the buffer to the preceding channel to the buffer to mix the portion of the aerosol with a freshly supplied aerosol; supplying the mixed aerosol into the buffer; and releasing the aerosol mixed in the buffer.

Like the apparatus, in the method, the pressure adjustment unit may be a Venturi tube. The pressure of the Venturi tube is lower than that of the buffer.

The buffer may have a capacity that corresponds to the volume of the aerosol that passes through the channel for a period of 0.1 to 100 times of a concentration change period of the aerosol.

BRIEF DESCRIPTION OF THE DRAWINGS

The above and other features and advantages of the present invention will become more apparent by describing in detail exemplary embodiments thereof with reference to the attached drawings in which:

FIG. 1 is a diagram that illustrates an example of an apparatus for stabilizing the concentration of an aerosol according to the present invention;

FIG. 2 is a graph that illustrates the concentration of a commonly prepared aerosol that does not pass through an apparatus for aerosol concentration stabilization of the present invention wherein the concentration of the aerosol is measured as the average concentration of the aerosol is increased by increasing a powder supply during the preparation of the aerosol.

DETAILED DESCRIPTION OF THE INVENTION

Figure 3:
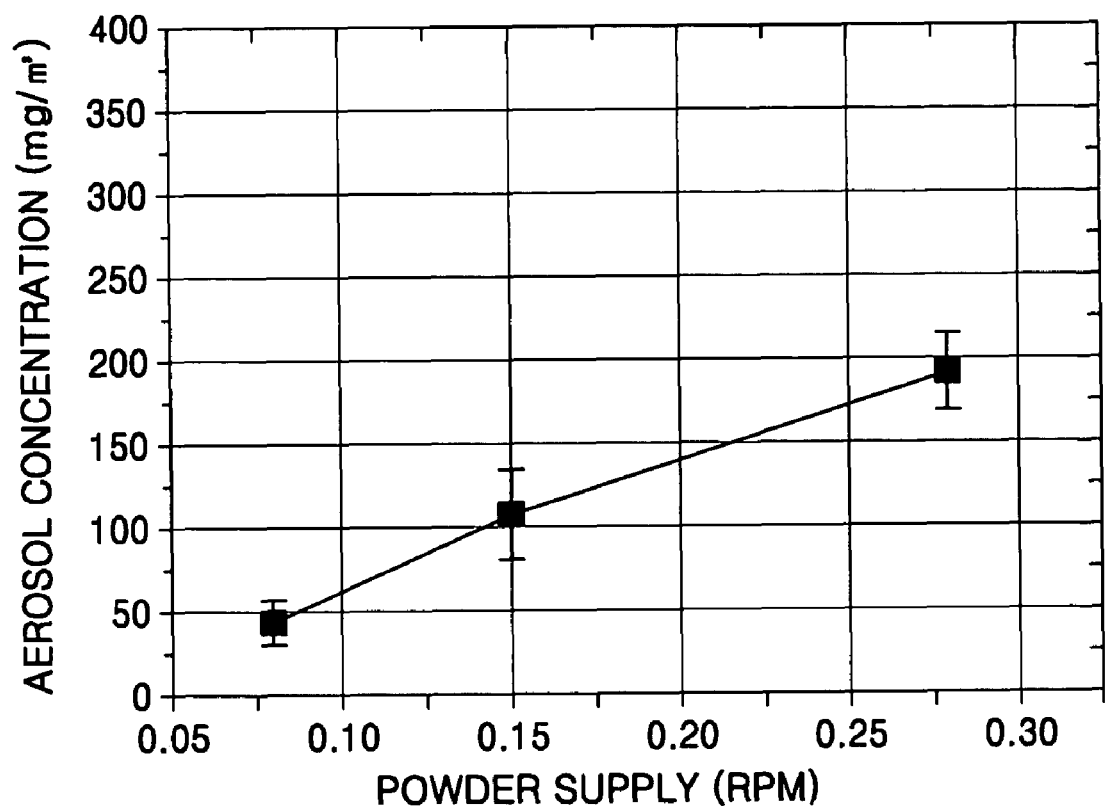
FIG. 3 is a graph that illustrates the concentration of a commonly prepared aerosol that is stabilized by an apparatus for aerosol concentration stabilization of the present invention wherein the concentration of the aerosol is measured as the average concentration of the aerosol is increased by increasing a powder supply during the preparation of the aerosol.

Hereinafter, the present invention will be described in more detail.

An apparatus for aerosol concentration stabilization of the present invention is an apparatus used to make uniform an average concentration of an aerosol over time.

Figures 1, 2:
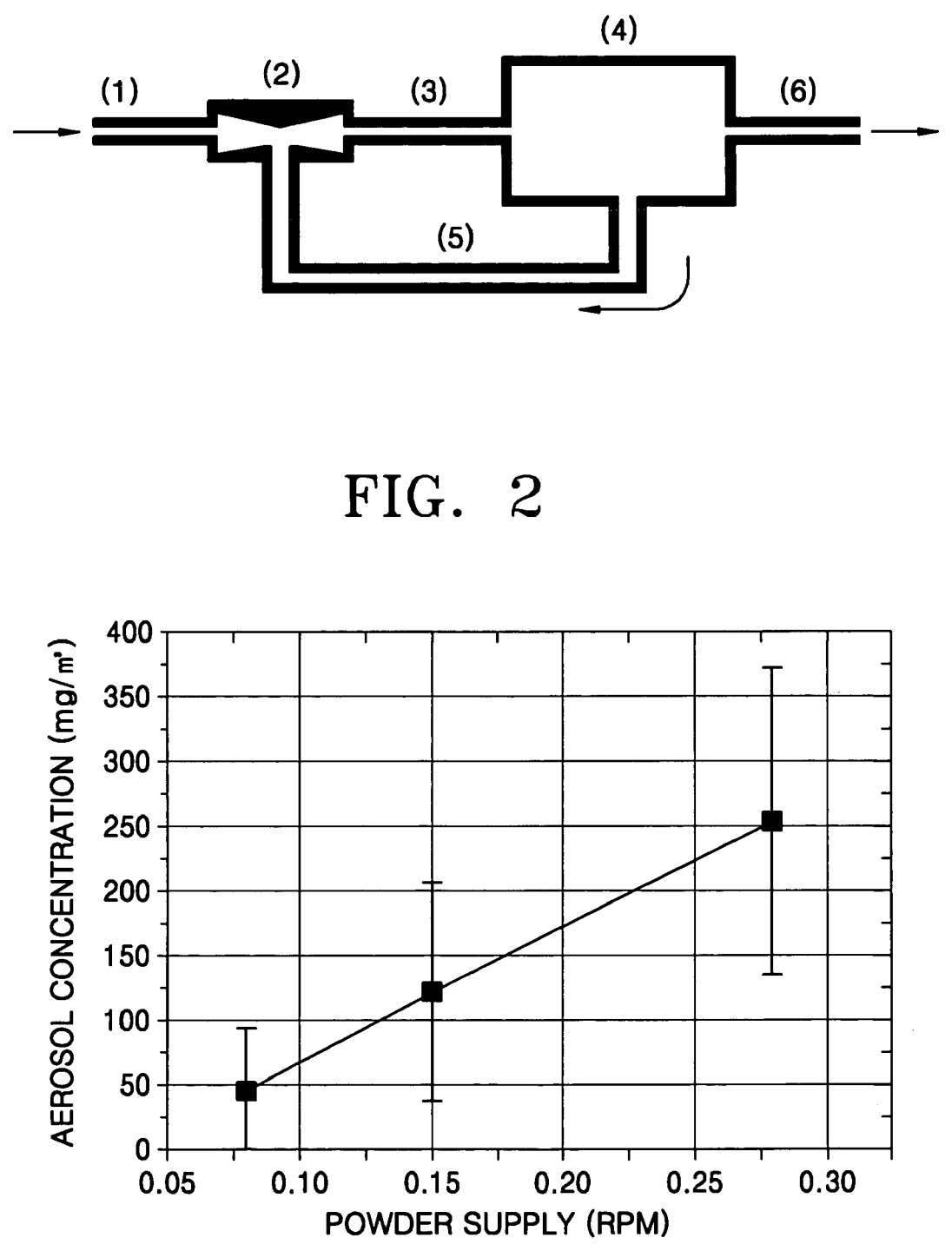

FIG. 1 is a diagram that illustrates an example of an apparatus for stabilizing the concentration of an aerosol according to the present invention. Referring to FIG. 1, a previously generated aerosol is supplied in an aerosol inlet channel 1. Here, the previously generated aerosol is an aerosol that changes periodically or non-periodically in its concentration over time.

The aerosol, which has been supplied in the aerosol inlet channel 1, is accelerated by an aerosol pressure adjustment unit 2 and then passes through an aerosol transport channel 3 extended from the aerosol pressure adjustment unit 2. The aerosol pressure adjustment unit 2 may be a Venturi tube. Various acceleration devices commonly known in the pertinent art may also be used. The pressure of the Venturi tube must be lower than that of a subsequent buffer 4.

The aerosol that has passed through the aerosol transport channel 3 comes in the buffer 4. The buffer 4 has a remarkably large sectional area, relative to the aerosol inlet channel 1 and the aerosol transport channel 3 commonly used for aerosol transportation. After suddenly reaching the buffer 4 with a large capacity, the aerosol is collected and mixed in the buffer 4. As a result, when the aerosol which has a differential concentration over time of aerosol generation during flow in the common-sized aerosol inlet and transport channels, reaches the buffer 4 with a large capacity, collection and mixing of the aerosol occur, which makes the concentration of a considerable volume of the aerosol uniform. The aerosol having a uniform concentration by the buffer 4 passes through a common-sized aerosol outlet channel 6. Therefore, a stabilized aerosol with a uniform concentration is obtained. Preferably, the buffer has a capacity that corresponds to the volume of the aerosol that passes through the aerosol inlet channel 1 and the aerosol transport channel 3 for a period of 0.1 to 100 times of a concentration change period of the incoming aerosol.

In addition, a portion of the aerosol present in the buffer 4 may be fed back to the preceding channel to the buffer 4, i.e., the aerosol inlet channel 1 or the aerosol transport channel 3 via a feedback channel 5, and mixed with a freshly supplied aerosol. Therefore, mixing of the aerosol can be more efficiently carried out. Furthermore, the volume of the aerosol present in the buffer 4 increases, thereby increasing the flow rate of the aerosol in the buffer 4. As a result, precipitation of powders or liquid droplets in the aerosol can be prevented. These effects can be accomplished by partial increase of the volume of the aerosol in the buffer 4 by the feedback. The aerosol fed back to the preceding channel to the buffer 4 via the feedback channel 5 is again mixed in the buffer 4 and then released via the aerosol outlet channel 6.

The present invention also provides a method for stabilizing the concentration of a previously generated aerosol. The method has the same principle as the above-described apparatus for aerosol concentration stabilization. The stabilized aerosol having a uniform concentration in this way can be used in preparation of nanoparticles. Generally, an aerosol containing solid powders or liquid droplets can be used as a material in nanoparticle preparation. For example, laser ablation of an aerosol containing solid powders can produce nanoparticles. In this case, the size of the nanoparticles largely depends on a laser condition, a pressure, and the concentration of the solid powders. In this respect, supply of an aerosol with a uniform concentration is very important in preparation of uniformly sized nanoparticles.

Hereinafter, the present invention will be described more specifically by Examples. However, the following Examples are provided only for illustrations and thus the present invention is not limited to or by them.

Comparative Example 1

Aerosols in which silicon powders were mixed with a nitrogen gas were prepared according to a conventional method. The aerosols were prepared in such a manner that the silicon powders were pressed to form cylindrical cakes which were then scraped off and mixed with the nitrogen gas. The silicon powders had an average particle size of 1 micron and the flow rate of the nitrogen gas was 1 liter/min. Wright II (BGI Inc.) was used as an aerosol generator.

The concentrations of the aerosols thus prepared were measured using a light scattering method. In detail, the concentrations of the aerosols were measured as the average concentrations of the aerosols were increased by increasing the supply of the powders during the preparation of the aerosol and the results are depicted in FIG. 2. In FIG. 2, the standard deviations of the concentrations of the aerosols measured per second for 10 minutes are also represented by error bars.

As shown in FIG. 2, as a powder supply increased, an aerosol concentration increased.

Example 1

Aerosols prepared in the same manner as in Comparative Example 1 were stabilized by an apparatus for aerosol concentration stabilization of the present invention and then the concentrations of the aerosols were measured. The concentrations of the aerosols were measured in the same conditions as in Comparative Example 1. A buffer with a capacity of 0.7 liter was used in the apparatus for aerosol concentration stabilization. The results are shown in FIG. 3. In FIG. 3, like in Comparative Example 1, the standard deviations of the concentrations of the aerosols measured per second for 10 minutes are also represented by error bars.

Discussion

In comparison between the graphs of FIGS. 2 and 3, when the same quantity of powders was supplied, the lengths of error bars in FIG. 3 were remarkably decreased, relative to those in FIG. 2. This means that a use of an apparatus of the present invention decreases a change in aerosol concentrations with time, thereby stabilizing aerosols.

At a powder supply rate of 0.28 RPM, an average aerosol concentration of Example 1 was slightly decreased, relative to that of Comparative Example 1. However, as a powder supply decreased, a decrease of the average aerosol concentration was little observed. In this respect, it can be seen that an apparatus of the present invention can decrease a change in aerosol concentrations over time without significantly decreasing an average aerosol concentration, thereby stabilizing aerosols.

As apparent from the above description, according to the present invention, a simple apparatus for aerosol concentration stabilization is added to a conventional aerosol generator. Thereby, the concentration of a previously generated aerosol can be maintained constant for a long-term and a short-term period without causing damage or deterioration of the aerosol. The aerosol thus stabilized can be used as a material for preparation of nanoparticles with uniform characteristics.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for stabilizing the concentration of a previously generated aerosol, the apparatus comprises:
   an aerosol inlet channel which receives an externally generated first aerosol including a gas and a particle suspended in the gas;
   an aerosol pressure adjustment unit which accelerates the externally generated first aerosol and is connected to the aerosol inlet channel;
   an aerosol transport channel connected to the aerosol pressure adjustment unit;

a buffer connected to the aerosol transport channel, wherein the buffer has a sectional area which is significantly larger than that of either the aerosol inlet channel or the aerosol transport channel;

an aerosol outlet channel connected to the buffer and an outside a feedback channel which is separate from the aerosol transport channel and the aerosol outlet channel and which connects the buffer and the aerosol pressure adjustment unit;

wherein the externally generated first aerosol accelerated by the aerosol pressure adjustment unit reaches the buffer via the aerosol transport channel and is fluidly mixed with a second aerosol having a different particulate density than the externally generated first aerosol in the buffer to generate a third aerosol, wherein the third aerosol is output to the outlet channel, and wherein the feedback channel feeds back a portion of the third aerosol present in the buffer to the aerosol transport channel.

2. The apparatus of claim 1, wherein the aerosol pressure adjustment unit is a Venturi tube.

3. The apparatus of claim 1, wherein the buffer has a capacity that corresponds to a volume of the aerosol which passes through the aerosol inlet channel and the aerosol transport channel for a period of a factor of about 0.1 times to about 100 times of a concentration change period of the aerosol.

4. The apparatus of claim 1, wherein the buffer is configured to fluidly mix the externally generated first aerosol and the second aerosol therein.

* * * * *